United States Patent [19]
Low

[11] Patent Number: 5,426,113
[45] Date of Patent: Jun. 20, 1995

[54] METHOD OF PREVENTING ULCER FORMATION CAUSED BY NONSTEROIDAL ANTIINFLAMMATORY DRUGS EMPLOYING TETRAZOL-BENZOTHIOPHENE CARBOXAMIDE COMPOUNDS

[75] Inventor: Joseph E. Low, Brighton, Mich.

[73] Assignee: Warner-Lambert Company, Morris Plains, N.J.

[21] Appl. No.: 224,891

[22] Filed: Apr. 8, 1994

[51] Int. Cl.⁶ ..................... A61K 31/41; A61K 31/38
[52] U.S. Cl. ..................... 514/381; 514/382; 514/444
[58] Field of Search ..................... 514/381, 382, 444

[56] References Cited

U.S. PATENT DOCUMENTS

| | | | |
|---|---|---|---|
| 4,703,053 | 10/1987 | Connor et al. | 514/382 |
| 4,910,317 | 3/1990 | Connor et al. | 514/381 |
| 4,931,459 | 6/1990 | Connor et al. | 514/381 |
| 5,290,798 | 3/1994 | Gillard et al. | 514/361 |

OTHER PUBLICATIONS

Gastroenterology May 1993;104: A137 "Gastric Cytoprotective Effect of CI-959 Against the Erosive Effects of Ethanol, Indomethacin and Aspirin in Rats" Joseph E. Low, et al.

*Primary Examiner*—Raymond Henley, III
*Assistant Examiner*—Ted Criares
*Attorney, Agent, or Firm*—Francis J. Tinney

[57] ABSTRACT

Tetrazol-benzothiophenes carboxamides or a pharmaceutically acceptable salt thereof are useful in preventing ulcer formation caused by nonsteroidal antiinflammatory drugs in mammals.

12 Claims, 6 Drawing Sheets

METHOD OF PREVENTING ULCER FORMATION CAUSED BY NONSTEROIDAL ANTIINFLAMMATORY DRUGS EMPLOYING TETRAZOL-BENZOTHIOPHENE CARBOXAMIDE COMPOUNDS

BACKGROUND OF THE INVENTION

The present invention relates to a medical method of treatment. More particularly, the present invention concerns the use of benzothiophene compounds, or a pharmaceutically acceptable salt thereof for the prevention of ulcer formation caused by nonsteroidal antiinflammatory drugs (NSAID) in a mammal. Particularly valuable is 5-methoxy-3-(1-methylethoxy)-N-1H-tetrazol-5-yl-benzo[b]thiophene-2-carboxamide.

Additionally, the present invention relates to pharmaceutical compositions which include these compounds and a pharmaceutically acceptable carrier for administering an effective amount of the aforementioned compounds in unit dosage form in the treatment method mentioned above.

NSAIDs are the most widely used drugs utilized for the treatment of rheumatic diseases (Agrawal N. M., et al., J. Rheumatol., 17:7-11, 1990). Although these agents can have significant beneficial effects by virtue of their antirheumatic and antiinflammatory effects, a significant side effect associated with this class of compounds is that they can cause gastrointestinal mucosal damage which may eventually lead to ulcers. The severity of this side effect can range from mild physical discomfort, to a discontinuation of the medication, or in the worst case of a bleeding ulcer, death of the patient.

Recently, it was reported in the literature (Wallace J. L., et al., Am. J. Physiol., 259:G462-467, 1990) that NSAID-induced gastric damage is a process not directly caused by NSAIDs but is indirectly mediated by neutrophils. Neutrophils are white blood cells (leukocytes) which normally reside and travel through blood vessels and provide the body with one of its defensive mechanisms against foreign infections. In the presence of local tissue stimulus such as that caused by a bacteria, adhesion receptors (P-selectin, E-selectin, intracellular cell adhesion molecule-1 (ICAM-1), etc.) are expressed locally on the walls of the blood vessels. These receptors interact with counter-receptors (L-selectin, macrophage receptor-1 (MAC-1), etc.) on the neutrophils allowing these cells to slow down via a rolling motion, stop and transmigrate into the tissue. This allows the offending bacteria to be attacked and killed by these migrating neutrophils. However, other stimulus such as that resulting from exposure to NSAIDs can also stimulate this adhesive event. In this case, normal tissue such as the gastric mucosa may be attacked inappropriately and damaged by the neutrophils.

Wallace, et al., have demonstrated that the NSAID-induced gastric damage can be prevented by either depleting the body of neutrophils or by blocking neutrophil adhesion using a monoclonal antibody directed against CD18, a component of the neutrophil adhesion molecule MAC-1 (Wallace J. L., et al., Gastroenterology, 100:878-883, 1991). These data highlight the pivotal role of neutrophil adhesion in the induction of NSAID related gastrointestinal damage.

U.S. Pat. No. 4,703,053, which is herein incorporated by reference, discloses certain benzothiophenes and benzofurans as antiallergy agents.

U.S. Pat. No. 4,910,317, which is herein incorporated by reference, discloses certain benzothiophenes and benzofurans as antiallergy agents, and in the treatment of cardiovascular disorders as well as antiinflammatory, antipsoriatic, antiulcer, and antimigraine agents.

U.S. Pat. No. 4,931,459, which is herein incorporated by reference, discloses certain benzothiophenes and benzofurans as agents for treating acute respiratory distress syndrome in humans.

Copending U.S. patent application Ser. No. 08/092,045 discloses the use of benzothiophenes and benzofurans as agents of therapeutic use in the treatment of inflammatory bowel disease.

It was recently discovered that 5-methoxy-3-(1-methylethoxy)-N-1H-tetrazol-5-yl-benzo[b]thiophene-2-carboxamide can inhibit neutrophil adhesion mediated by the adhesion molecule MAC-1 (Wright C. D., et al., Keystone symposium, P226, Feb. 20-26, 1994).

5-Methoxy-3-(1-methylethoxy)-N-1H-tetrazol-5-yl-benzo[b]thiophene-2-carboxamide inhibitory effect on the adhesion molecule MAC-1 is accompanied by its gastric cytoprotective effects against the damage caused by NSAIDs, such as indomethacin, and aspirin in rats (Low J. E., et al., Gastroenterology, 104:A137, 1993).

Thus, the object of the present invention is a medical method of treatment for the prevention of ulcer formation caused by NSAIDs with known benzothiophene compounds disclosed in U.S. Pat. No. 4,703,053.

SUMMARY OF THE INVENTION

Accordingly, a first embodiment of the present invention provides a method of treatment for the prevention of ulcer formation caused by nonsteroidal antiinflammatory drugs in mammals in need thereof which comprises administering to such mammal an effective amount of a compound of Formula I

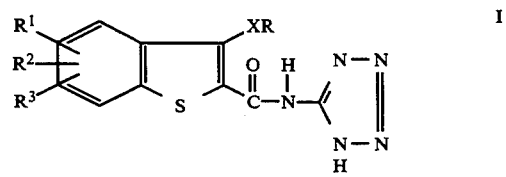

wherein
X is O, S, SO, or $SO_2$;
R is alkyl, phenyl, or benzyl; and
$R^1$, $R^2$, and $R^3$ are each the same or different and each is hydrogen, hydroxy, alkyl, alkoxy, thioalkoxy, halogen,

wherein
$R^4$ and $R^5$ are each the same or different and each is hydrogen or alkyl, or $NO_2$; or
a pharmaceutically acceptable salt thereof.

A still further embodiment of the present invention is a method of treatment for the prevention of ulcer formation caused by nonsteroidal antiinflammatory drugs in mammals in need thereof which comprises administering to such mammal an effective amount of a compound of Formula I in combination with a nonsteroidal antiinflammaory drug.

Finally, the present invention is directed to a pharmaceutical composition for administering an effective amount of a compound of Formula I in unit dosage form in the treatment methods mentioned above.

DETAILED DESCRIPTION OF THE INVENTION

Figure 1:
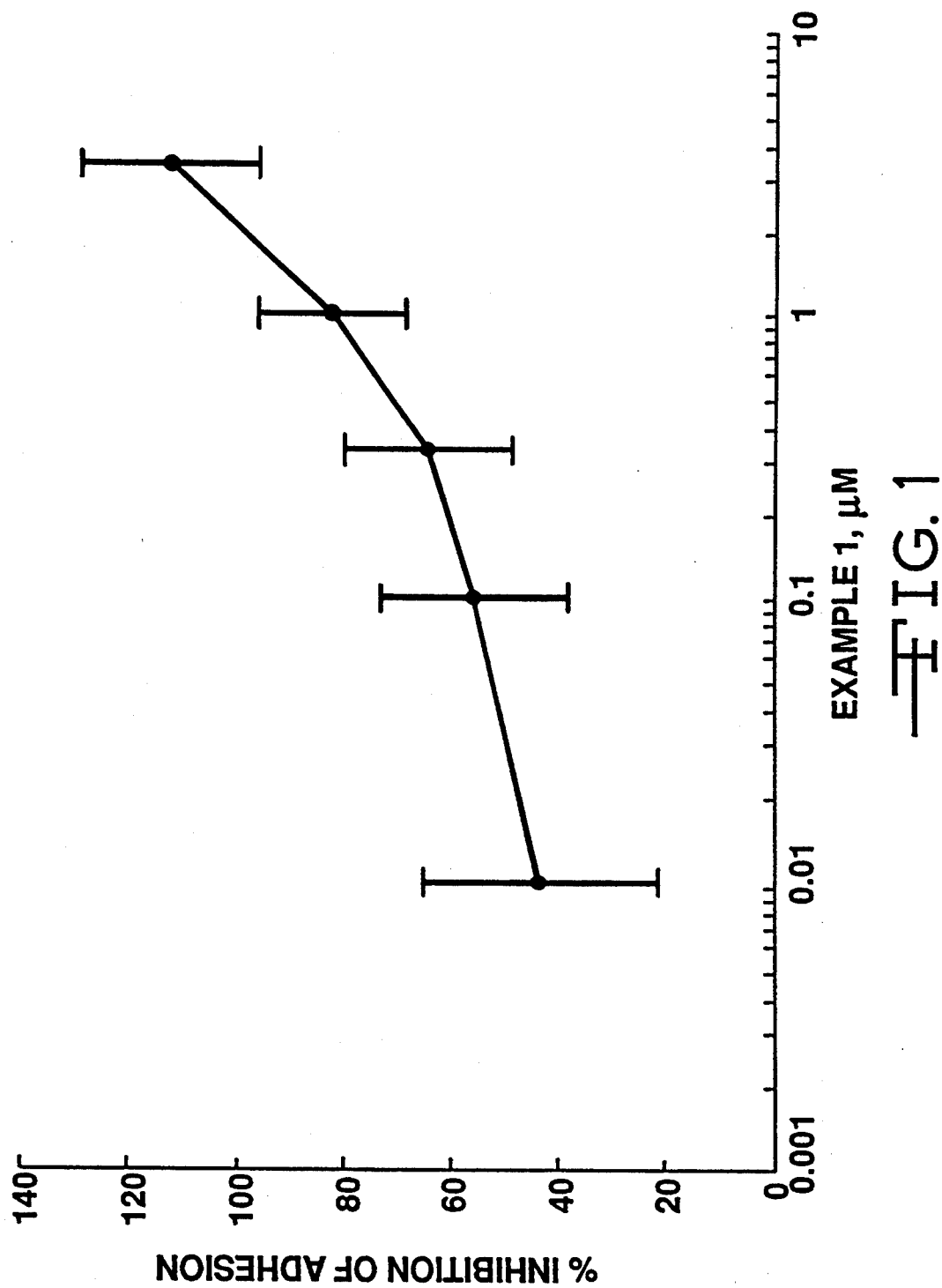
FIG. 1 is a plot of Example 1 inhibition of MAC-1 mediated adhesion of FMLP-stimulated neutrophils to KLH.

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The terms "alkoxy" and "thioalkoxy" are O-alkyl or S-alkyl as defined above for alkyl.

"Halogen" is fluorine, chlorine, bromine, or iodine.

The term "nonsteroidal antiinflammatory drug" (NSAID) means a drug that typically inhibits cyclooxygenation of arachidonic acid and thereby inhibits prostaglandin formation, for example, aspirin, magnesium salicylate, choline salicylate, choline magnesium salicylate, sodium salicylate, salicylsalicylic acid, diclofenac, diflunisal, fenoprofen, flurbiprofen, ibuprofen, indomethacin, ketoprofen, meclofenamate sodium, naproxen sodium, piroxicam, sulindac, tolmetin, etodolac, nabumetone, and the like. This term is described in Lombardino J. G., *Nonsteroidal Antiinflammatory Drugs*, Wiley-Interscience, John Wiley & Sons, New York, N.Y., 1985.

The term "ulcer" means a lesion on the surface of the skin or a mucous surface, caused by the superficial loss of tissue, usually with inflammation.

The term "gastric cytoprotection" means the prevention of gastric mucosal damage without the inhibition of acid secretion (Roberts, et al., *Gastroenterology*, 77:433–443, 1979).

The term "mammal" includes humans.

The compounds of Formula I are capable of further forming pharmaceutically acceptable base addition salts. All of these forms are within the scope of the present invention.

Pharmaceutically acceptable base addition salts of the compounds of Formula I are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma. Sci.*, 66:1, 1977).

The base addition salts of said acidic compounds are prepared by contacting the free acid form with a sufficient amount of the desired base to produce the salt in the conventional manner. Preferably, a compound of Formula I can be converted to a base salt by treating with an aqueous solution of the desired base, such that the resulting pH is greater than 9. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred compound of Formula I used in the methods of the present invention is one wherein $R^1$, $R^2$, and $R^3$ is 5-methoxy, 6-methoxy, or 5,6-dimethoxy.

Particularly valuable are:

5-Methoxy-3-(1-methylethoxy)-N-1H-tetrazol-5-yl-benzo[b]thiophene-2-carboxamide (Example 1);

6-Methoxy-3-(1-methylethoxy)-N-1H-tetrazol-5-yl-benzo[b]thiophene-2-carboxamide (Example 2);

5,6-Dimethoxy-3-(1-methylethoxy)-N-1H-tetrazol5-yl-benzo[b]thiophene-2-carboxamide (Example 3);

5,6-Dimethoxy-3-phenoxy-N-1H-tetrazol-5-yl-benzo[b]thiophene-2-carboxamide (Example 4);

3,5-Dimethoxy-N-1H-tetrazol-5-yl-benzo[b]thiophene-2-carboxamide (Example 5);

3-(1-Methylethoxy)-N-1H-tetrazol-5-yl-benzo[b]thiophene-2-carboxamide (Example 6);

5-Methoxy-3-[(1-methylethyl)thio]-N-1H-tetrazol-5-yl-benzo[b]thiophene-2-carboxamide (Example 7);

5-Methoxy-3-phenoxy-N-1H-tetrazol-5-yl-benzo[b]thiophene-2-carboxamide (Example 8); and 6-Methoxy-3-phenoxy-N-1H-tetrazol-5-yl-benzo[b]thiophene-2-carboxamide (Example 9); or a pharmaceutically acceptable salt thereof.

A most preferred compound of Formula I is:

5-Methoxy-3-(1-methylethoxy)-N-1H-tetrazol-5-yl-benzo[b]thiophene-2-carboxamide (Example 1); or a pharmaceutically acceptable salt thereof.

Particularly valuable nonsteroidal antiinflammatory drugs used in the second embodiment of the present invention are: aspirin, magnesium salicylate, choline salicylate, choline magnesium salicylate, sodium salicylate, salicylsalicylic acid, diclofenac, diflunisal, fenoprofen, flurbiprofen, ibuprofen, indomethacin, ketoprofen, meclofenamate sodium, naproxen sodium, piroxicam, sulindac, tolmetin, etodolac, and nabumetone.

The compounds of Formula I are described and claimed in U.S. Pat. No. 4,703,053, which issued Oct. 27, 1987, and U.S. Pat. No. 4,910,317 which issued Mar. 20, 1990. The compounds of Formula I and pharmaceutically acceptable salts thereof are described in U.S. Pat. No. 4,703,053 beginning at column 1, line 50 through column 2, line 11 and in U.S. Pat. No. 4,910,317 beginning at column 1, line 49 through column 2, line 2.

The method of synthesis of the compounds of Formula I is described in U.S. Pat. No. 4,703,053 at column 2, lines 12 to 68; column 3, lines 1 to 28 and in U.S. Pat. No. 4,910,317 at column 2, lines 39 to 67; column 3, lines 1 to 26 and lines 48 to 68; column 4, lines 1 to 68; and column 5, lines 1 to 4.

The compounds of Formula I are valuable agents for preventing ulcer formation caused by NSAIDs. The tests employed indicate that the compounds of Formula I possess the ability to prevent ulcer formation caused by NSAIDs.

A. Inhibitory Effects on Neutrophil Adhesion

Wright C. D., et al., (Keystone symposium, P226, Feb. 20-26, 1994) reported that 5-methoxy-3-(1-methylethoxy)-N-1H-tetrazol-5-yl-benzo[b]thiophene-2-carboxamide inhibits neutrophil adhesion mediated by the adhesion molecule MAC-1. In these in vitro studies, treatment of neutrophils with $10^{-8}$M of the stimulus N-formyl-methionyl-leucyl-phenylalanine (FMLP) for 1 hour at 37° C. resulted in a 49% increase of MAC-1 dependent adherence to keyhole limpet hemocyanin (KLH)-coated plastic. Pretreatment of the neutrophils with Example 1 inhibited the FMLP-stimulated neutrophil adhesion to KLH-coated plates with an $IC_{50}$ of 0.02 $\mu$M (FIG. 1).

Figure 2:
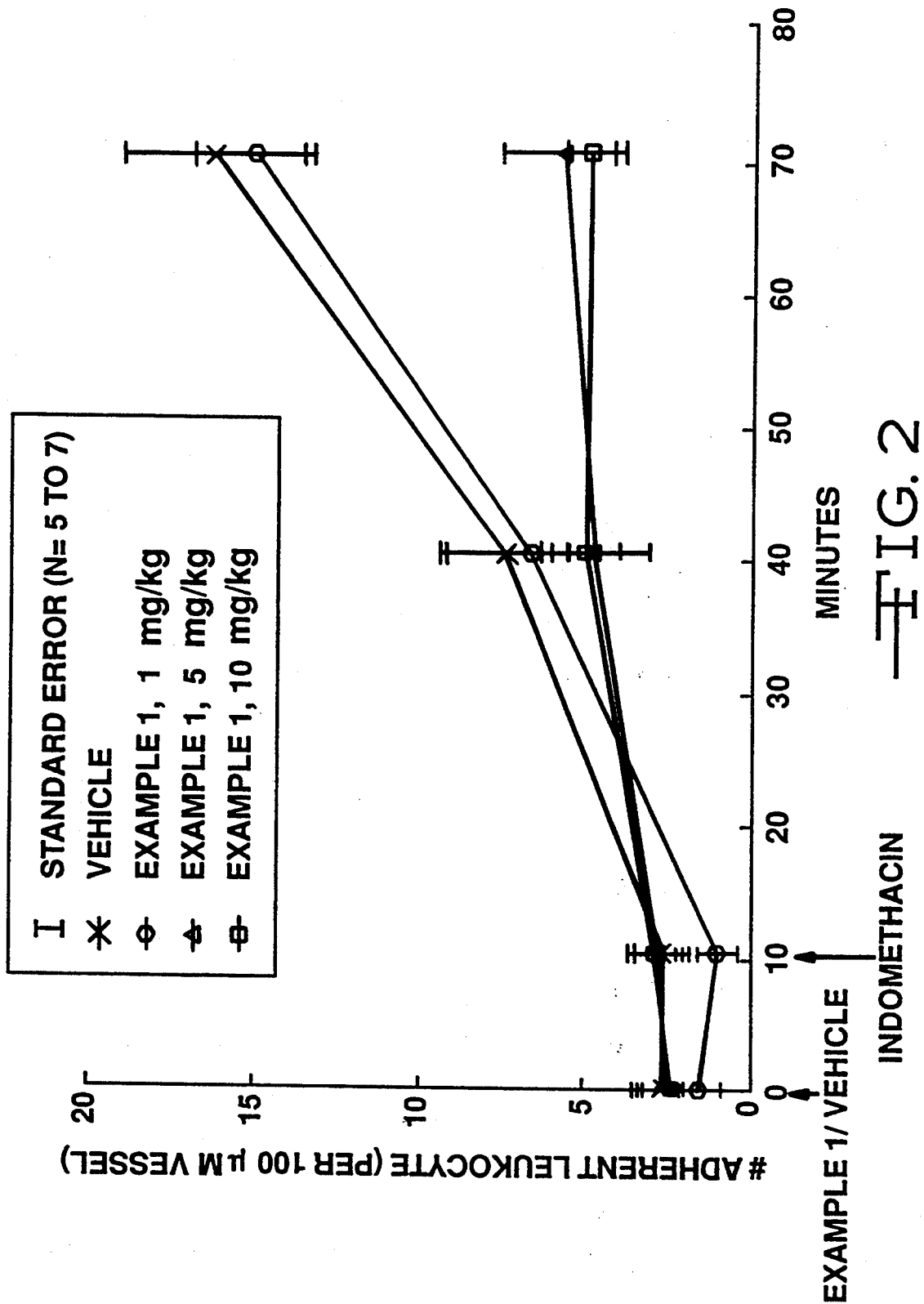
FIG. 2 is a plot of Example 1 inhibition of NSAID-stimulated adhesion of rat neutrophil in post-capillary venules in vivo.

In addition, the ability of Example 1 to inhibit NSAID-induced adhesion of leukocytes in vivo was also demonstrated. In these studies, oral treatment of rats with the NSAID indomethacin results in leukocyte adhesion in the animal's mesenteric post-capillary venules. This can be observed and measured using the technique of Intravital microscopy. As seen in FIG. 2, oral administration of the drug vehicle (control group) at the zero time point followed by oral indomethacin treatment 10 minutes later results in increasing numbers of leukocyte adhesion at the 40 and 70 minute time point. Pretreatment of the animals with 1 mg/kg PO of Example 1 at the zero time point resulted in no protective effects. However, complete inhibition of leukocyte adhesion was achieved with the 5 or 10 mg/kg PO dose of Example 1.

B. Gastric Cytoprotection

Figure 3:
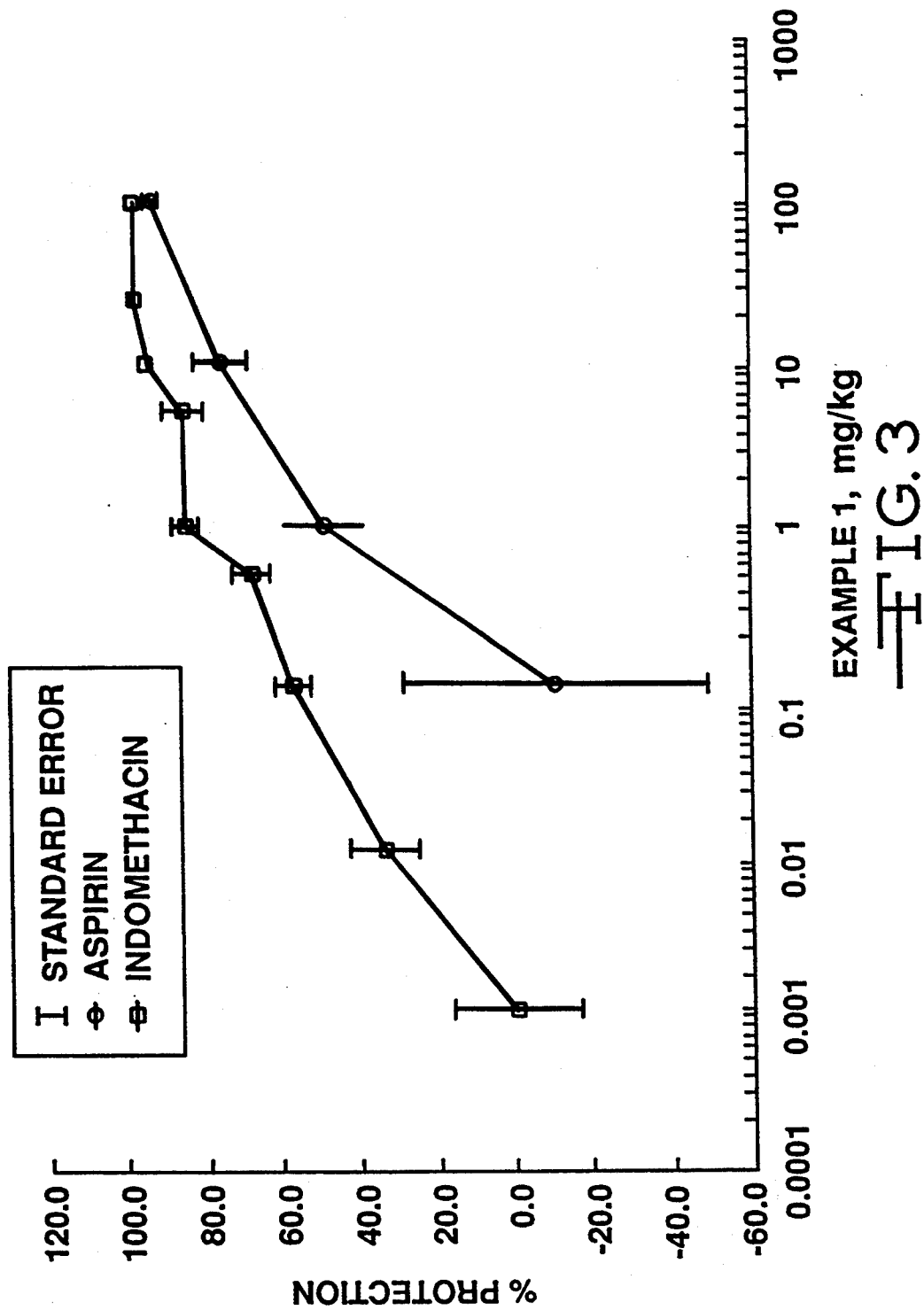
FIG. 3 is a plot of the dose-response curve for the cytoprotective effect of Example 1 against NSAID-induced gastric damage in vivo.

To confirm that inhibition of neutrophil adhesion can protect against NSAID-induced gastric damage, Example 1 was tested in two in vivo rat NSAID-induced gastric damage models (FIG. 3) (Low J. E., et al., Gastroenterology, 104:A137, 1993). Rats were pretreated with different oral doses of Example 1 ranging from 0.001 to 100 mg/kg. Fifteen minutes later, the animals were orally challenged with a single dose of 20 mg/kg indomethacin or 288 mg/kg aspirin. The animals were euthanized either at 4 hours (indomethacin) or 30 minutes (aspirin) later and the amount of gastric damage was assessed using image analysis. As can be seen, Example 1 is a very potent and orally active cytoprotective agent with $ED_{50}$s of 1 mg/kg for indomethacin and 0.01 mg/kg for aspirin.

Figure 4:
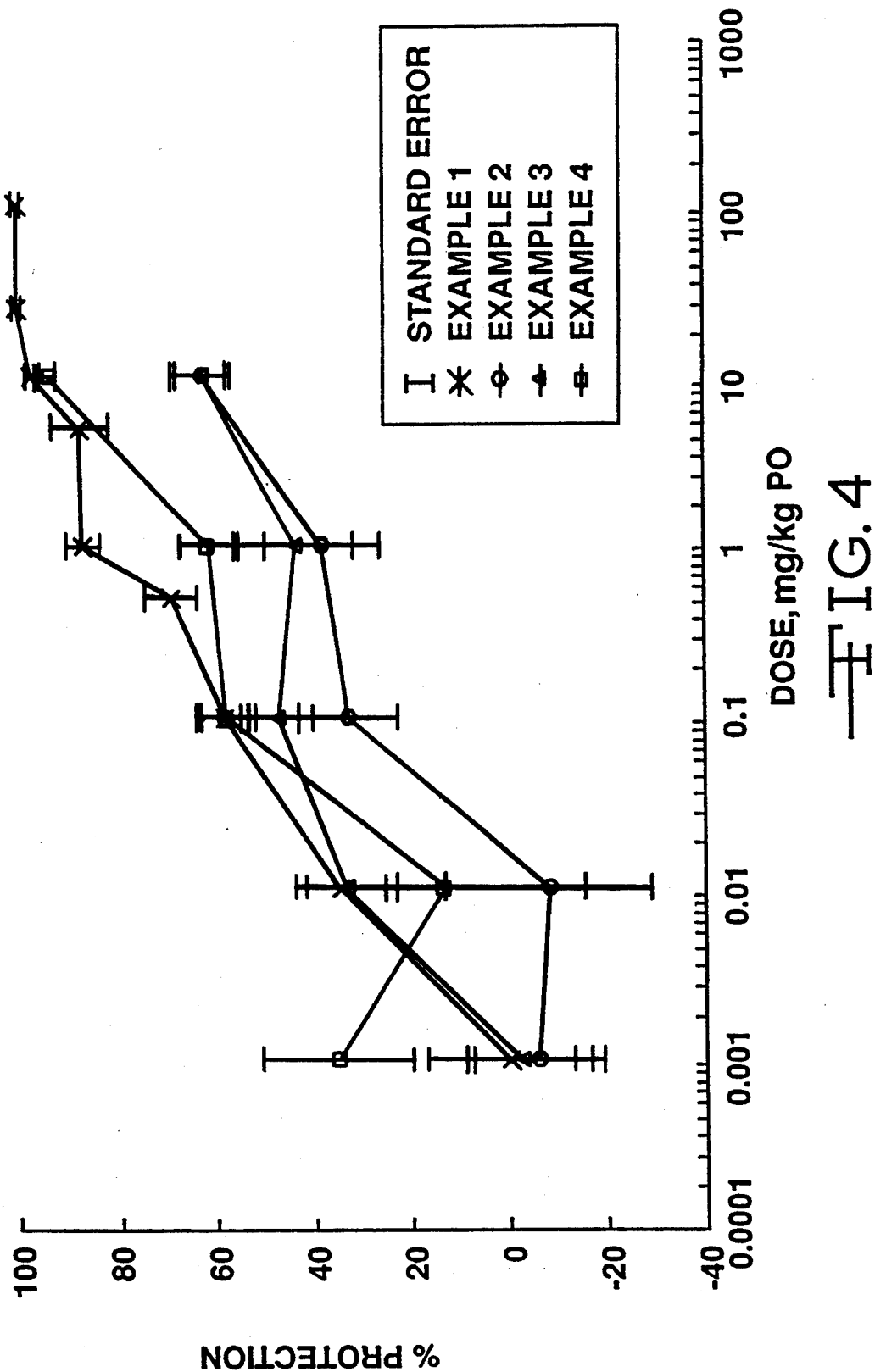
FIG. 4 is a plot of gastric cytoprotective effects of selective compounds of Formula I in the aspirin erosion model.

Additional compounds of Formula I were tested in both the MAC-1 and the aspirin-induced gastric damage model (Table 1 and FIG. 4). Compounds which were active in the MAC-1 assay were also active in the gastric cytoprotective assay.

To qualify as a gastric cytoprotective agent, it has also been determined that Example 1 does not inhibit gastric acid secretion. This has been tested in two different animal models. In the rat, Example 1 was tested in the Shay rat model of basal acid secretion. Rats were administered orally either vehicle, 50 or 200 mg/kg of Example 1. One hour later the animals were anesthetized and the pyloric sphincter to the stomach was ligated. The stomachs were removed 4 hours later and their acid content determined. Example 1 was found to have no effect on basal acid secretion.

The effect of Example 1 on stimulated acid secretion was examined in the dimaprit-stimulated gastric fistula beagle dog model (Russell J., et al., Drug Development Research, 10:69-74, 1987). Constant intravenous administration of the highly specific histamine $H_2$-receptor agonist dimaprit (0.2 mg/kg hr) resulted in stimulated gastric mucus/acid secretion and the maintenance of a constant and low (pH=1.0) gastric secretion pH. Pretreatment of the animals with a 1.5 mg/kg PO dose of the positive control ranitidine (histamine $H_2$-receptor antagonist), resulted in 75% to 90% decrease in gastric secretion during the first 2.5 hours, a 60% to 70% decrease in titratable acidity, increased in pH by 4 units, and a reduction of total acid output (product of volume and concentration) by 70% to 90%. Pretreatment with 0.1, 1.0, or 10 mg/kg PO of Example 1 resulted in no significant changes in gastric secretion. All parameters of gastric secretion appeared to be practically identical to those observed in the vehicle-only controls. In conclusion, compounds of Formula 1 do not appear to affect stimulated acid secretion.

C. Selective Active Transport Into Gastrointestinal Tissue

Figure 5B:
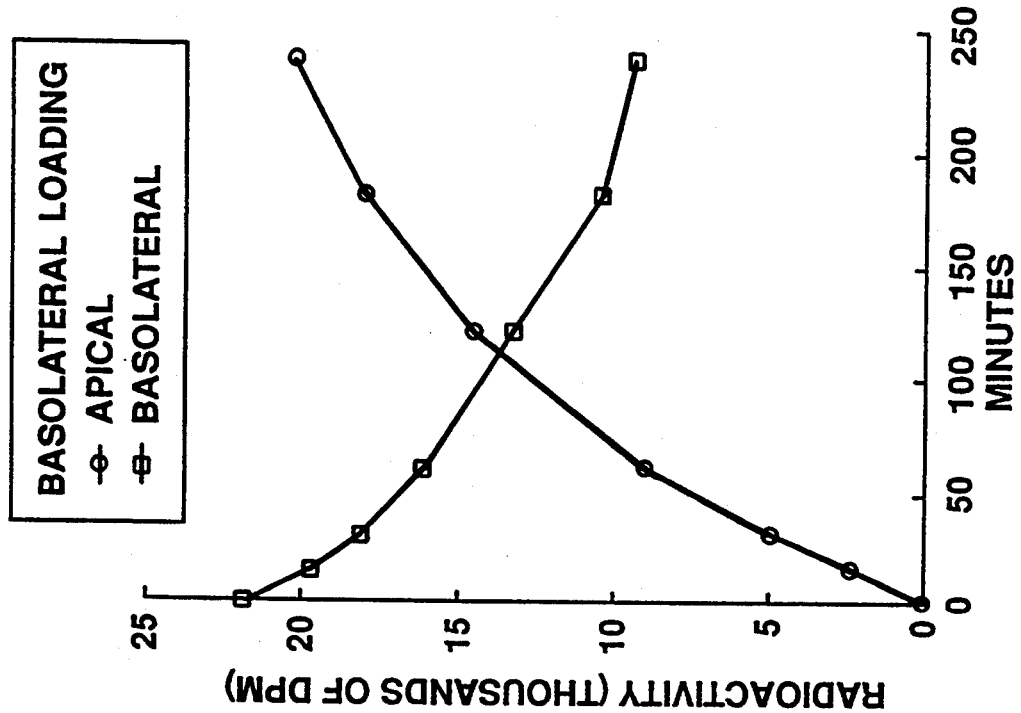
FIG. 5 is a plot of transport of Example 1 across CaCO-2 monolayer.
Figure 5A:
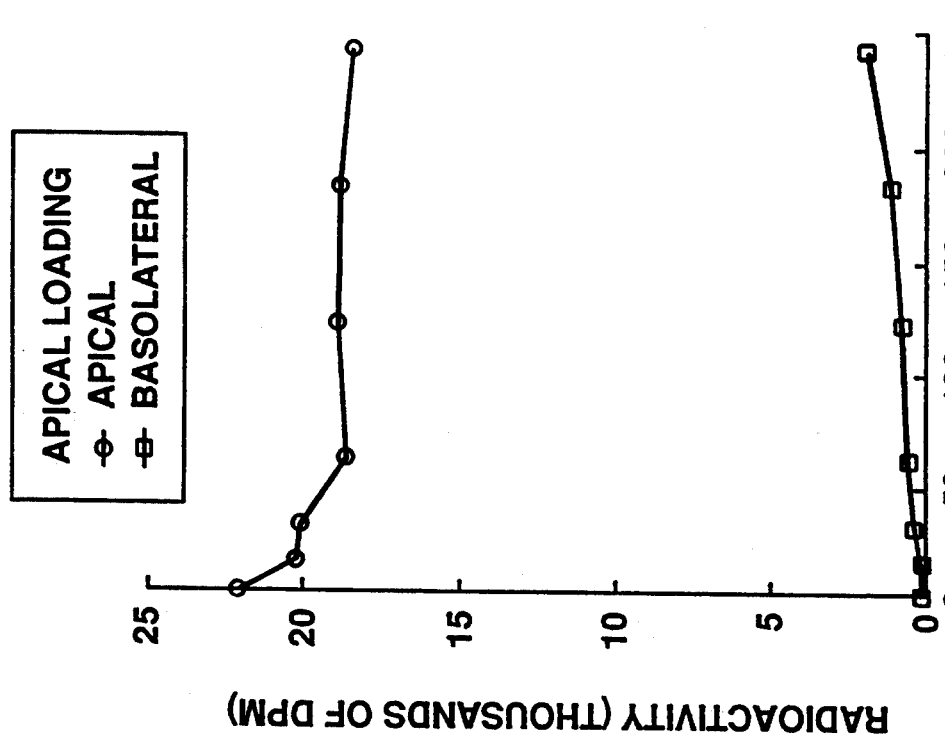

Apart from the effect on cell adhesion, the compounds of Formula I have the ability to be actively transported into gastrointestinal tissues. Thus, intravenous administration of radiolabeled Example 1 followed by whole body autoradiographic studies has demonstrated that there is a rapid (5 minutes) and high levels of radiolabeled material associated with gastrointestinal tissues (stomach, small and large intestines). Secondly, in vitro studies conducted with human colonic adenocarcinoma (CaCO-2) cells have demonstrated that Example 1 is selectively and actively transported by these cells. [$^{14}$C]Example 1 (22.9 $\mu$g/mL) was loaded on to either the apical (luminal) or basolateral (vascular) of the monolayer. Samples were obtained over 250 minutes from either side of the chamber in each experiment. As can be seen in FIG. 5, when Example 1 was loaded on the apical side, there is a slow diffusion of material across the monolayer with most of the material remaining on the apical side. In contrast, when Example 1 was initially loaded on the basolateral side, there was an active transport of this material to the apical side. Four hours after the start of the experiment, there was significantly more Example 1 on the apical side compared to the basolateral side strongly suggesting an active process of secretion. This data suggest that Example 1 in the systemic circulation can be actively transported into the lumen of the gastrointestinal tract. This characteristic increases local drug concentration in gastrointestinal tissues resulting in enhanced pharmacological activity and selectivity for these tissues.

D. Plasma Protein Binding and Effect on Pharmacological Potency

Figure 6:
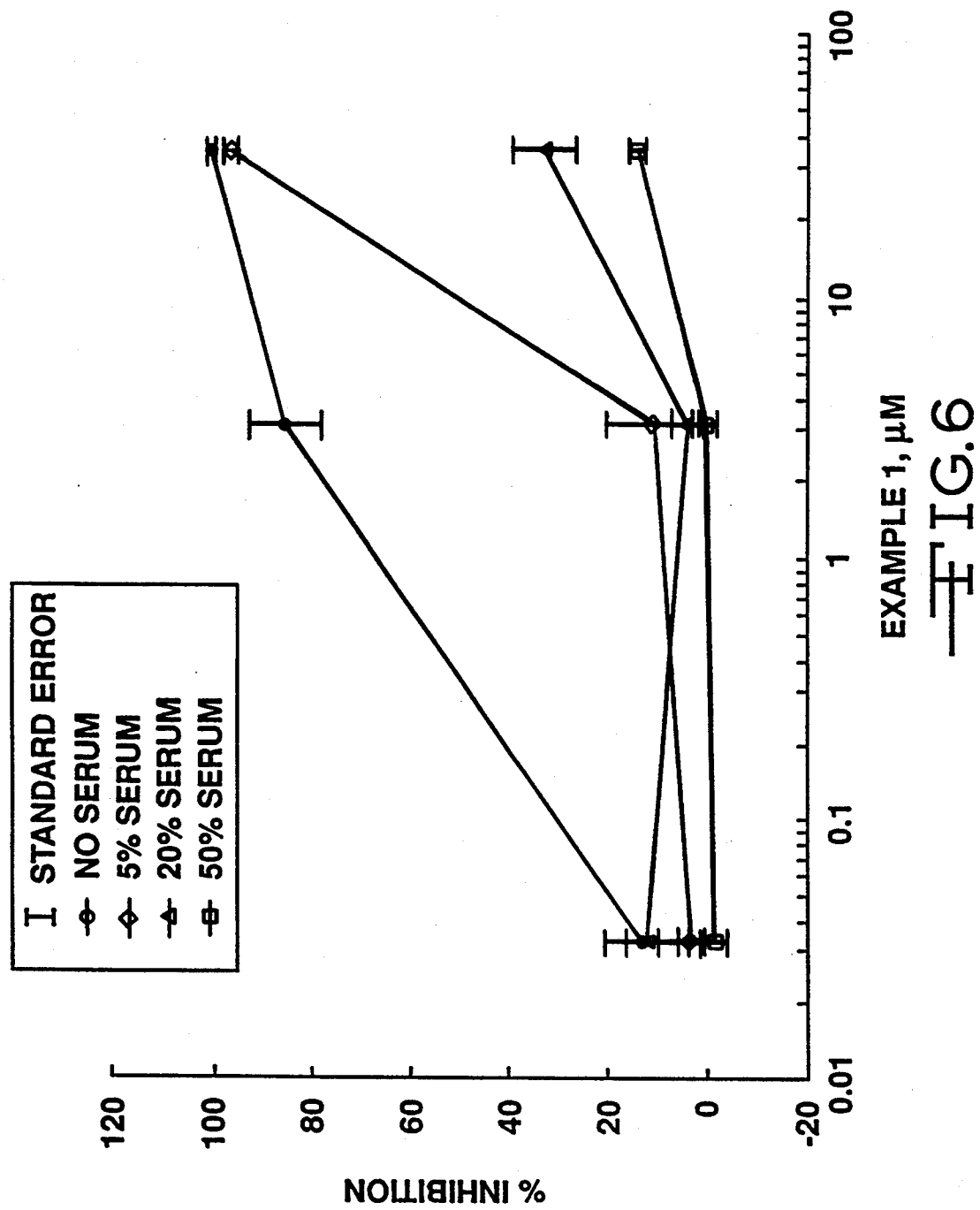
FIG. 6 is a plot of Example 1 inhibitory effect on human basophil histamine release.

Apart from gastric cytoprotection, Example 1 has demonstrated pharmacological activity in a variety of animal disease models (asthma, allergy, arthritis, adult respiratory distress syndrome (ARDS), and cardiac reperfusion). The $ED_{50}$ doses required to demonstrate pharmacological activity in these models are relatively high and range from 30 to 100 mg/kg PO to 5 to 20 mg/kg IV. In contrast, the $ED_{50}$ for gastric cytoprotection in animal models range from 0.01 to 1 mg/kg PO. The reason for the significantly higher $ED_{50}$s required for the non-gastric cytoprotection indications may be due to serum protein binding. Example 1 is highly bound (98–99%) by plasma protein from a variety of mammals (rat, dog, sheep, and human). The presence of plasma protein has also been shown to significantly attenuate pharmacological activity in vitro. The inhibitory effect of Example 1 on human basophil histamine release stimulated with anti-IgE is shown in FIG. 6. In the absence of serum, Example 1 has an $IC_{50}$ of 0.3 μM. However, in the presence of increasing concentration of serum (5–50%), the inhibitory effect of Example 1 is significantly reduced. Since Example 1 is actively transported and concentrated in the gastrointestinal tissue by the previously mentioned active transport mechanism, this may overcome the effect of serum protein binding. In turn, this may be responsible for the greater potency of Example 1 in diseases associated with gastrointestinal tissues.

In summary, the aforementioned results show that the compounds of Formula I have the ability to prevent ulcer formation caused by NSAIDs.

TABLE 1

Relationship Between Anti-MAC-1 and Gastric Cytoprotective Effect of Benzothiophenes

| Example | Compound | Anti-MAC-1 Activity ($IC_{50}$, μM) | Gastric Cytoprotective Effect ($ED_{50}$, mg/kg PO) |
|---|---|---|---|
| 1 | 5-Methoxy-3-(1-methylethoxy)-N-1H-tetrazol-5-yl-benzo[b]thiophene-2-carboxamide | 0.02 | 0.01 |
| 2 | 6-Methoxy-3-(1-methylethoxy)-N-1H-tetrazol-5-yl-benzo[b]thiophene-2-carboxamide | <3.3 | 1 |
| 3 | 5,6-Dimethoxy-3-(1-methylethoxy)-N-1H-tetrazol-5-yl-benzo[b]thiophene-2-carboxamide | 1.3 | 1 |
| 4 | 5,6-Dimethoxy-3-phenoxy-N-1H-tetrazol-5-yl-benzo[b]thiophene-2-carboxamide | <3.3 | 0.01 |

Additionally, the compounds of Formula I may be combined with a nonsteroidal antiinflammatory drug such as aspirin, magnesium salicylate, choline salicylate, choline magnesium salicylate, sodium salicylate, salicylsalicylic acid, diclofenac, diflunisal, fenoprofen, flurbiprofen, ibuprofen, indomethacin, ketoprofen, meclofenamate sodium, naproxen sodium, piroxicam, sulindac, tolmetin, etodolac, and nabumetone, and the like for the prevention of ulcer formation caused by nonsteroidal antiinflammatory drugs.

Finally, the compounds of Formula I are valuable agents for the prevention of ulcer formation caused by ethanol.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, intrarectally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.5 mg to 100 mg preferably 0.5 mg to 50 mg according to the particular application and the potency of the active component. The composition can, if desired, also contain other compatible therapeutic agents.

In therapeutic use as agents to prevent ulcer formation caused by nonsteroidal antiinflammatory drugs, the compounds of Formula I utilized in the pharmaceutical method of this invention are administered at the initial dosage of about 0.01 mg to about 2 mg/kg four times a day (QID). A daily dose range of about 0.01 mg to about 1 mg/kg four times a day (QID) is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Nonsteroidal antiinflammatory drugs utilized in the second embodiment of the present invention are used in standard dosage amounts known in the art. For example, dosages of these agents are disclosed in *Medical Letter*, Vol. 33, Jul. 12, 1991; *Medical Letter*, Vol. 33, Aug. 23, 1991; and Friedel H. A., et al., *Drugs*, 45:131-156 (1993).

I claim:

1. A method for preventing gastrointestinal ulcer formation caused by nonsteroidal antiinflammatory drugs by inhibition of neutrophil adhesion in mammals in need thereof which comprises administering to such mammal an effective amount of a compound Formula I

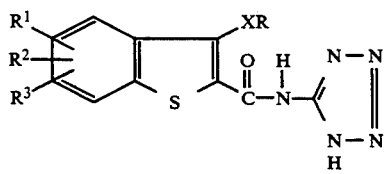

wherein
X is O, S, SO, or SO$_2$;
R is alkyl, phenyl, or benzyl; and
R$^1$, R$^2$, and R$^3$ are each the same or different and each is hydrogen, hydroxy, alkyl, alkoxy, thioalkoxy, halogen,

wherein
R$^4$ and R$^5$ are each the same or different and each is hydrogen or alkyl, or NO$_2$; or
a pharmaceutically acceptable salt thereof.

2. The method of claim 1, wherein in a compound of Formula I
R$^1$, R$^2$, and R$^3$ is 5-methoxy, 6-methoxy, or 5,6-dimethoxy.

3. The method of claim 1 wherein a compound of Formula I is selected from the group consisting of:
5-Methoxy-3-(1-methylethoxy)-N-1H-tetrazol-5-yl-benzo[b]thiophene-2-carboxamide;
6-Methoxy-3-(1-methylethoxy)-N-1H-tetrazol-5-yl-benzo[b]thiophene-2-carboxamide;
5,6-Dimethoxy-3-(1-methylethoxy)-N-1H-tetrazol-5-yl-benzo[b]thiophene-2-carboxamide;
5,6-Dimethoxy-3-phenoxy-N-1H-tetrazol-5-yl-benzo[b]thiophene-2-carboxamide;
3,5-Dimethoxy-N-1H-tetrazol-5-yl-benzo[b]thiophene-2-carboxamide;
3-(1-Methylethoxy)-N-1H-tetrazol-5-yl-benzo[b]thiophene-2-carboxamide;
5-Methoxy-3-[(1-methylethyl)thio]-N-1H-tetrazol-5-yl-benzo[b]thiophene-2-carboxamide;
5-Methoxy-3-phenoxy-N-1H-tetrazol-5-yl-benzo[b]thiophene-2-carboxamide; and
6-Methoxy-3-phenoxy-N-1H-tetrazol-5-yl-benzo[b]thiophene-2-carboxamide; or a pharmaceutically acceptable salt thereof.

4. The method of claim 1 wherein the compound of Formula I is:
5-Methoxy-3-(1-methylethoxy)-N-1H-tetrazol-5-benzo[b]thiophene-2-carboxamide;
or a pharmaceutically acceptable salt thereof.

5. The method of claim 1 wherein the compound of Formula I is:
5-Methoxy-3-(1-methylethoxy)-N-1H-tetrazol-5-yl-benzo[b]thiophene-2-carboxamide monosodium salt.

6. The method of claim 1 wherein a compound of Formula I is administered orally.

7. The method of claim 1 wherein the compound of Formula I is administered orally in a dose of about 0.01 to about 2 mg/kg four times a day.

8. A method for preventing gastrointestinal ulcer formation caused by nonsteroidal antiinflammatory drugs by inhibition of neutrophil adhesion in mammals in need thereof which comprises administering to such mammal an effective amount of a compound of Formula I

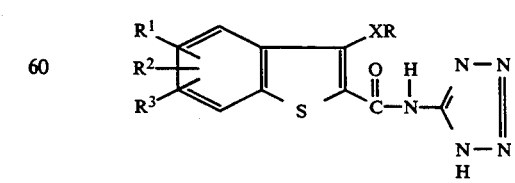

wherein
X is O, S, SO, or SO$_2$;
R is alkyl, phenyl, or benzyl; and

R¹, R², and R³ are each the same or different and each is hydrogen, hydroxy, alkyl, alkoxy, thioalkoxy, halogen,

wherein

R⁴ and R⁵ are each the same or different and each is hydrogen or alkyl, or NO₂; or a pharmaceutically acceptable salt thereof in combination with a nonsteroidal antiinflammatory drug.

9. The method of claim 8, wherein in a compound of Formula I

R¹, R², and R³ is 5-methoxy, 6-methoxy, or 5,6-dimethoxy.

10. The method of claim 8 wherein the compound of Formula I is selected from the group consisting of:

5-Methoxy-3-(1-methylethoxy)-N-1H-tetrazol-5-yl-benzo[b]thiophene-2-carboxamide;

6-Methoxy-3-(1-methylethoxy)-N-1H-tetrazol-5-yl-benzo[b]thiophene-2-carboxamide;

5,6-Dimethoxy-3-(1-methylethoxy)-N-1H-tetrazol-5-yl-benzo[b]thiophene-2-carboxamide;

5,6-Dimethoxy-3-phenoxy-N-1H-tetrazol-5-yl-benzo[b]thiophene-2-carboxamide;

3,5-Dimethoxy-N-1H-tetrazol-5-yl-benzo[b]thiophene-2-carboxamide;

3-(1-Methylethoxy)-N-1H-tetrazol-5-yl-benzo[b]thiophene-2-carboxamide;

5-Methoxy-3-[(1-methylethyl)thio]-N-1H-tetrazol-5-yl-benzo[b]thiophene-2-carboxamide;

5-Methoxy-3-phenoxy-N-1H-tetrazol-5-yl-benzo[b]thiophene-2-carboxamide; and

6-Methoxy-3-phenoxy-N-1H-tetrazol-5-yl-benzo[b]thiophene-2-carboxamide; or a pharmaceutically acceptable salt thereof.

11. The method of claim 8 wherein the compound of Formula I is:

5-Methoxy-3-(1-methylethoxy)-N-1H-tetrazol-5-benzo[b]thiophene-2-carboxamide; or a pharmaceutically acceptable salt thereof.

12. The method of claim 8 wherein the compound of Formula I is:

5-Methoxy-3-(1-methylethoxy)-N-1H-tetrazol-5-yl-benzo[b]thiophene-2-carboxamide monosodium salt.

* * * * *

UNITED STATES PATENT AND TRADEMARK OFFICE
CERTIFICATE OF CORRECTION

PATENT NO. : 5,426,113
DATED      : June 20, 1995
INVENTOR(S) : Low

It is certified that error appears in the above-indentified patent and that said Letters Patent is hereby corrected as shown below:

Column 9, line 52, insert the word "of" before "Formula".

Column 10, line 38 at the end of the line, "5-ben-" should read "5-yl-ben-".

Column 12, line 18 at the end of the line, "5-ben-" should read "5-yl-ben-".

Signed and Sealed this

Seventeenth Day of October, 1995

Attest:

BRUCE LEHMAN

*Attesting Officer*   *Commissioner of Patents and Trademarks*